(12) United States Patent
Lundgren

(10) Patent No.: US 6,881,060 B2
(45) Date of Patent: Apr. 19, 2005

(54) SUCTION TUBE WITH A SIEVE

(75) Inventor: Dan Lundgren, Hovås (SE)

(73) Assignee: Bladhs Medical AB, Bredaryd (SE)

( * ) Notice: Subject to any disclaimer, the term of this patent is extended or adjusted under 35 U.S.C. 154(b) by 0 days.

(21) Appl. No.: 10/385,734

(22) Filed: Mar. 12, 2003

(65) Prior Publication Data
US 2004/0014002 A1 Jan. 22, 2004

(51) Int. Cl.⁷ .............................................. A61C 17/06
(52) U.S. Cl. ..................................................... 433/91
(58) Field of Search .............................. 433/91, 92, 95, 433/96; 210/416.1, 435, 436, 446; 604/35, 902

(56) References Cited

U.S. PATENT DOCUMENTS

| | | | | |
|---|---|---|---|---|
| 4,265,621 A | * | 5/1981 | McVey | 433/91 |
| 4,393,879 A | * | 7/1983 | Milgrom | 600/571 |
| 4,878,900 A | * | 11/1989 | Sundt | 604/119 |
| 5,078,603 A | | 1/1992 | Cohen | |
| 5,195,952 A | * | 3/1993 | Solnit et al. | 604/19 |
| 5,630,939 A | * | 5/1997 | Bulard et al. | 210/416.1 |
| 5,688,121 A | | 11/1997 | Davis | |
| 5,779,649 A | * | 7/1998 | Herbert | 600/571 |
| 6,183,254 B1 | * | 2/2001 | Cohen | 433/92 |
| 6,280,415 B1 | * | 8/2001 | Johnson | 604/118 |

FOREIGN PATENT DOCUMENTS

DE 3316397 A1 1/1985

* cited by examiner

Primary Examiner—Todd E. Manahan
(74) Attorney, Agent, or Firm—Steven S. Payne

(57) ABSTRACT

A device in a suction tube to be connected to a suction conduit for surgical or dental use to separate from the suction flow entrained particulate material. The suction tube being open at both ends and has a sieve element located therein. The sieve is inclined in relation to the axial direction of the suction tube in order that separated material shall be collected in a pocket formed at the suction end of the suction tube.

8 Claims, 5 Drawing Sheets

SUCTION TUBE WITH A SIEVE

BACKGROUND OF THE INVENTION

1. Field of the Invention

The present invention relates to a device in a suction tube for surgical or dental use to be connected with a suction conduit, for separating from the suction flow particulate material entrained therein, the suction tube being opened at both ends and has a sieve element located therein.

At surgical operations in bone tissue, for example such operations as are performed in the mouth cavity for different purposes such as fixation of tooth protheses of different types, bone is worked for fastening titanium screws or the like, which are used as anchoring elements. It is desired to take care of tissue fragments which at the working are detached for example as bone chips because these can be used for filling cavities existing in the bone tissue. At the operation a suction device is used in order to remove blood, saliva, and other liquid collected at the operation site. Then, the tissue fragments are sucked away and can get lost if they are not separated from the collected liquid flow. When working in the mouth cavity it is also important to collect metal fragments, for example gold chips, at grinding of bridges and crowns, or amalgam which has been drilled from teeth or is spilt when filling a tooth cavity. The sieve element also prevents screws and other small components used in implant constructions, or gold and porcelain inserts or crowns to be accidentally sucked into the suction system.

2. Description of the Prior Art

U.S. Pat. No. 5,688,121 discloses a flexible suction tube which at the outlet end has a disc-shaped filter element attached in the suction tube for separating amalgam from the suction flow. The filter element is attached in a ring which in turn is attached in the suction tube, so that the plane of the filter element is located across the flow, i.e. perpendicularly to the longitudinal axis of the suction tube.

A similar filter device is disclosed in U.S. Pat. No. 5,078,603. The filter is mounted in a suction tube for one way use so that it is scrapped after having been used on a patient, the disgusting handling in connection with cleaning of the filter thus being avoided.

However, these solutions as far as they are used in surgical and dental applications both cause clogging of the filter element because the material that has been separated will collect on the filter and will block the passage through the suction tube via the filter.

BRIEF SUMMARY OF THE INVENTION

The purpose of the invention is to provide a device of the kind referred to above by which total clogging of the filter is prevented.

The purpose is achieved by a device according to the invention wherein the sieve element according to claim 1 is inclined in relation to the axial direction of the suction tube.

In a particularly preferred embodiment of the invention the sieve has at the inner end thereof as seen in the direction of the suction flow, a non-perforated portion for collection of separated particulate material in a pocket formed between said portion and the inside surface of the suction tube.

In order to increase further the usefulness of the suction tube of the invention the sieve element according to a further development is located in a separate insert which is demountably connected to the inlet end of the suction tube, preferably with slide fit.

Further features of the invention are defined in the dependent claims.

BRIEF DESCRIPTION OF THE DRAWINGS

The invention will be described below in more detail, reference being made to embodiments shown in the accompanying drawings, in which.

DETAILED DESCRIPTION OF THE INVENTION

Figure 1:
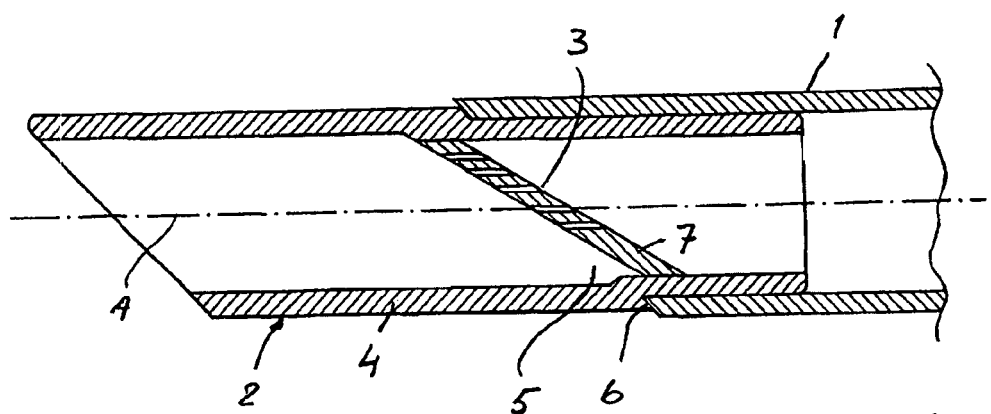
FIG. 1 is longitudinal cross-sectional view through a forward portion of a suction tube provided with an insert with a sieve.
Figure 2:
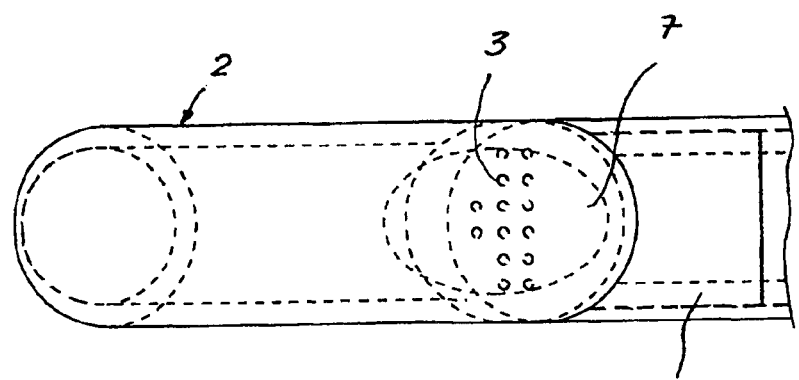
FIG. 2 is a plan view of the sieve insert of the suction tube of FIG. 1.

FIG. 1 discloses fragmentarily an extruded suction tube 1 having an axis A and an inlet end which is cut at an angle of about 45°. A tubular insert 2 has light slide fit in the inlet end of the suction tube 1 in order to be easily separated from and inserted into the suction tube. At the other end, not shown, the suction tube 1 shall be connected to a suction pipe.

The insert 2 has a sieve element 3 mounted therein. It is inclined about 30° in relation to the axis A the inlet portion 4 of the insert as a consequence thereof in front of the sieve element 3 forms a pocket 5 tapering in the flow direction, between the inside surface of portion 4 and the sieve element 3. Since the sieve insert 2 can be separated from the suction tube 1 it can easily be exchanged, if required. The sieve insert 2 forms at the outside thereof a circumferential shoulder 6 which abuts the obliquely cut end of the suction tube 1 and defines the axial and rotated positions of the sieve insert 2 in relation to the suction tube 1. Also the muzzle end of the sieve insert is obliquely cut, and in the disclosed rotated position of the insert in relation to the suction tube the muzzle end of the sieve insert is substantially parallel with the muzzle end of the suction tube.

Since the inlet end of the sieve insert 2 is obliquely cut it is easy to hold the suction tube 1 in a comfortable working position with the muzzle of the sieve insert 2 close to the site where suction is to be performed.

Due to the fact that the sieve element 3 located in the sieve insert 2 is inclined in the manner mentioned above material to be separated will be collected at the very back of the pocket 5 so that the sieve element 3 is prevented from being completely or partly clogged and thus from blocking the suction flow.

The sieve element 3 can be perforated over the total surface or over a major or minor portion of the surface. In the embodiment shown an inner end portion of the sieve element, as seen in the flow direction, is not perforated over about ⅓ of the surface of the sieve element 3 so that the sieve element has an unperforated lower portion 7 in order that the separated material shall be more easily collected in the pocket 5. This is particularly the case when under the suction operation the suction tube is oriented such that the sieve element 3 will slope inwardly and downwardly the collection being supported by gravity as well as the turbulent flow passing immediately above the pocket 5.

Figure 3:
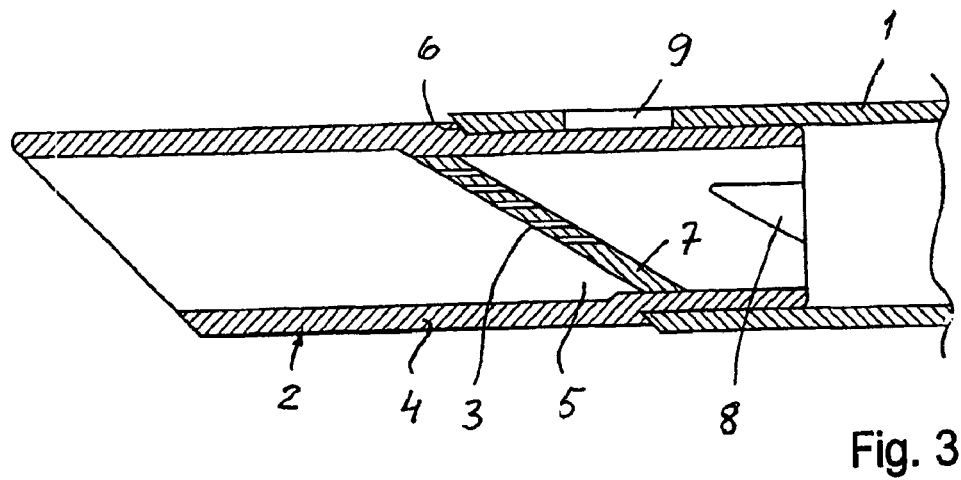
FIG. 3 is a longitudinal cross-sectional view corresponding to FIG. 1 wherein an aperture has been made in the wall of the suction tube behind the sieve and the sieve insert is provided with a slot such that a controllable stray flux can be provided by rotating the insert.

The alternative embodiment of the sieve insert shown in FIG. 3 allows the suction force to be controlled. For this purpose the sieve insert 2 behind the sieve element 3 as seen in the flow direction is provided with a lateral aperture 8, FIG. 3, or several apertures 8, FIG. 4 and can be rotated about the geometric longitudinal axis of the section tube in order to bring the aperture(s) 8 to overlap more or less a lateral aperture 9 in the suction tube 1 by rotation of the sieve insert 2 on the shoulder 6 of the sieve insert so that the insert will be displaced into or out of the suction tube in dependence of the rotational direction, a major or minor flow being sucked into the suction tube via apertures 8 and 9 as a stray flux. As a consequence thereof the suction force through the sieve 3 will be reduced to a corresponding degree. By providing the stray flux behind the sieve 3 the risk of for example bone material separated and collected on the sieve being dried out, is reduced, which improves the usefulness of the separated material. The apertures 8 preferably are located on both sides of the sieve insert 2 so that the rotational direction when controlling the suction flow is of no importance as long as one remembers the direction in which the sieve insert 2 initially was rotated in relation to the suction tube. In order to facilitate this it may be suitable to have some form of marking on elements 1 and 2, respectively.

In FIGS. 5 to 8 the suction tube 1 at the outlet end forms a connection socket 10 for a suction hose (not shown). Along a part of the suction tube 1 there is a longitudinal slot 11 in the tube wall. The sieve insert 2 is axially displaceable in the suction tube 1, and the sieve 3 is located at the inlet end of the sieve insert. A button 12 located on the outside of the suction tube is introduced through the slot 11 and is fixed to the sieve insert.

Figure 4:
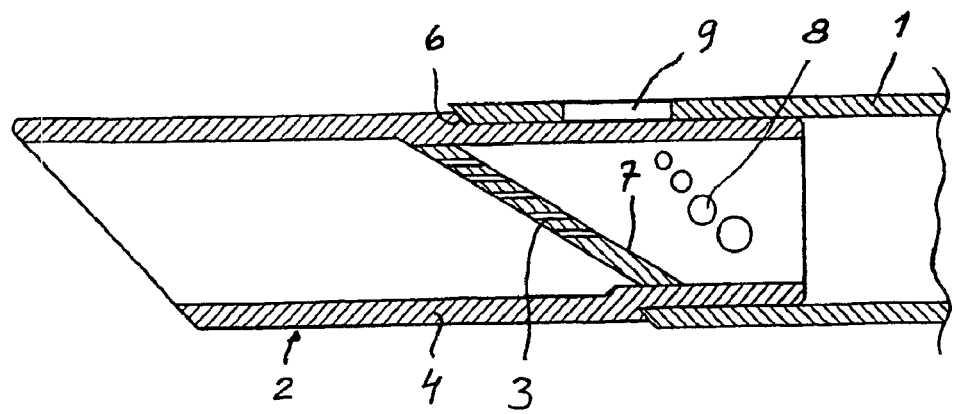
FIG. 4 is a longitudinal cross-sectional view corresponding to FIG. 3 wherein the stray flux slot of the sieve insert has been replaced by several apertures having a diameter of successively increasing dimension.
Figure 5:
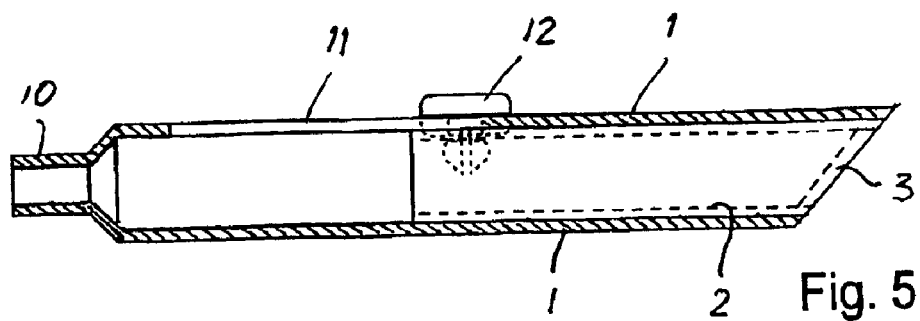
FIGS. 5 and 6 are a longitudinal cross-sectional view view and a plan view, respectively, of a suction tube with an alternative embodiment of the sieve insert.
Figure 6:
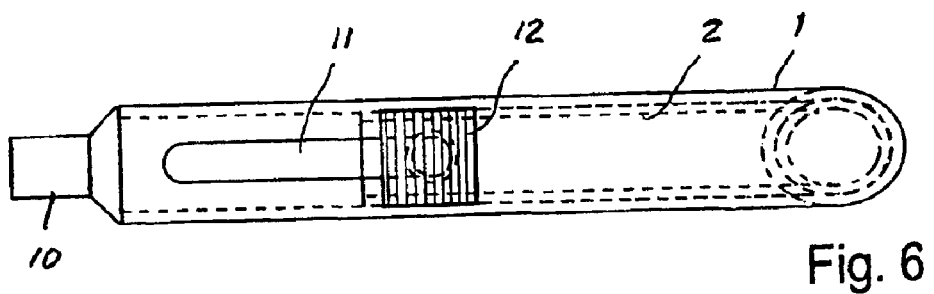

The slot 11 in this embodiment has the some function has the lateral apertures 8 in the embodiments according to FIGS. 3 and 4, viz. to provide a suction force control. It is possible to displace by means of the button 12 the sieve insert 2 along the slot 11 such that the open portion of the slot will be adjusted, which influences the suction force at the inlet end of the suction tube.

Figure 7:
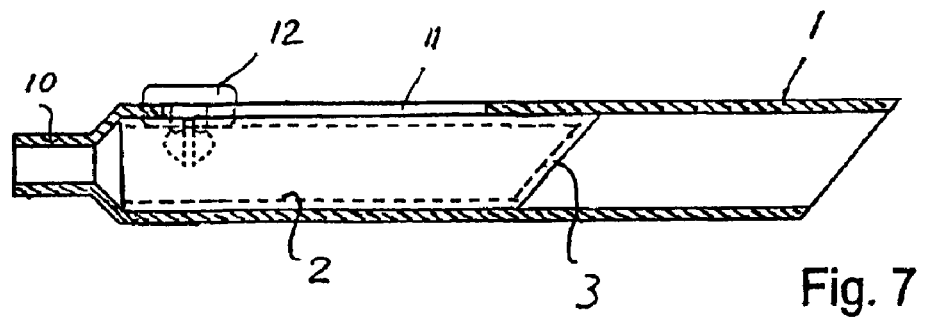
FIGS. 7 and 8 are views similar to FIGS. 5 and 6, respectively, but with the sieve insert in another adjusted position.
Figure 8:
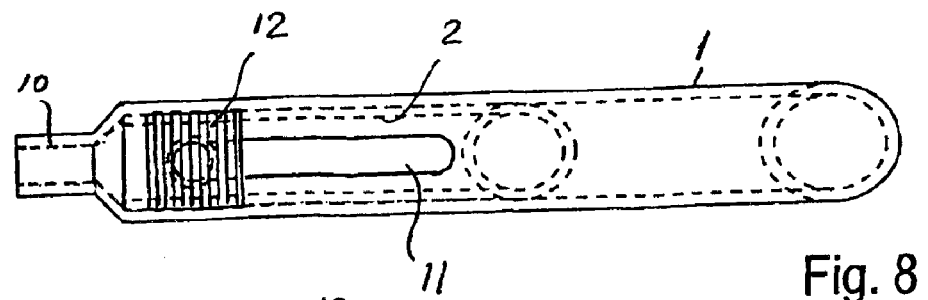
Figure 9:
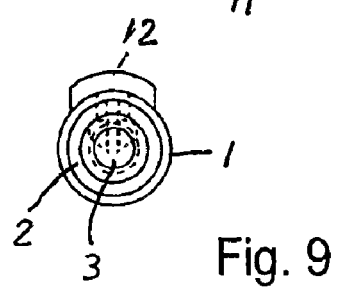
FIG. 9 is an end view of the muzzle of the suction tube of any of FIGS. 5 to 8.

By displacement of the sieve insert into the suction tube, the cavity 5 is created in which sucked up material can be temporarily collected. When such collection has taken place and it is desired to take care of the material the button is displaced to the outmost position thereof in which the sieve is in the same plane as the end 11 of the suction tube. This makes it easy to scrape off the collected material, and then the suction work can be resumed. In FIGS. 7 and 8 the button 12 has been moved back so that the sieve insert 2 is in the innermost position thereof in the suction tube 1. In this position the suction force is at maximum, i.e. there is no stray flux through the slot 11.

Figure 12:
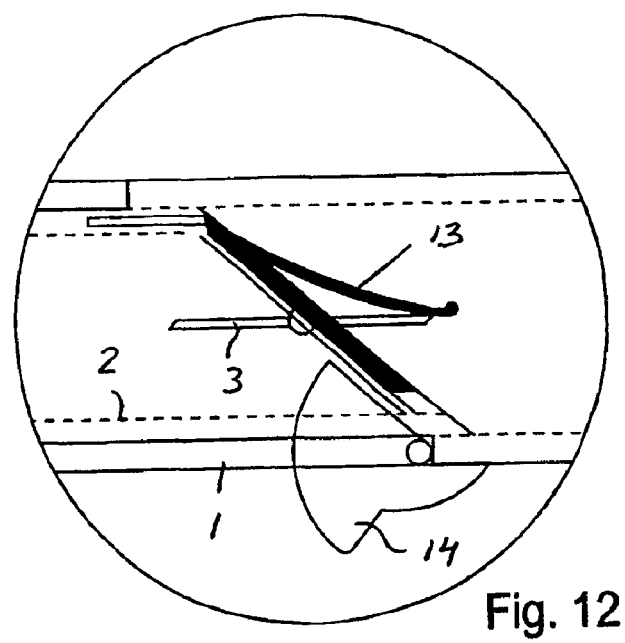
FIG. 12 is an enlarged view of the portion surrounded by a circle in FIG. 10.
Figure 10:
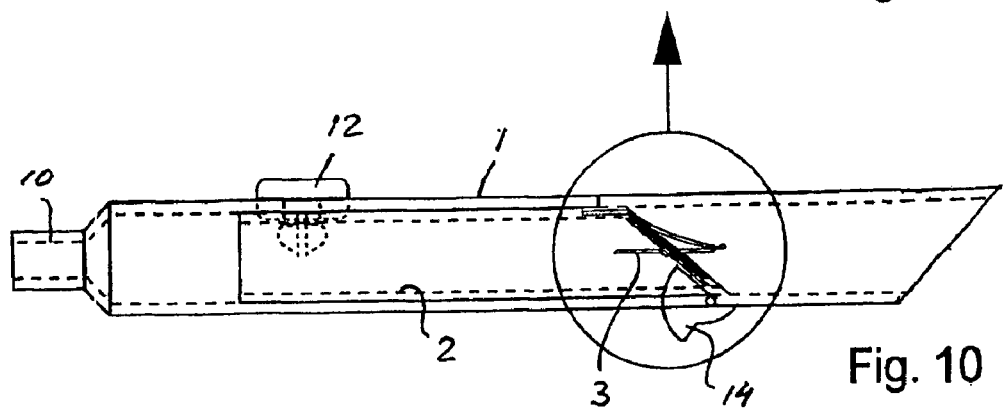
FIGS. 10 and 11 are a side view and a plan view, respectively, of a suction tube with a further embodiment of the sieve insert the insert being shown in different adjusted positions.
Figure 11:
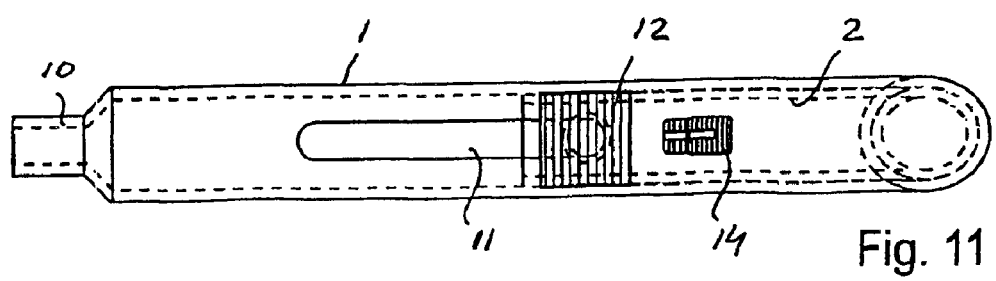
Figure 13:
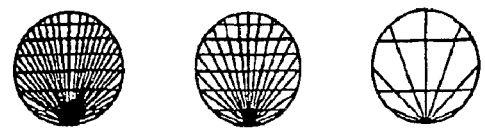
FIG. 13 is plan views of alternative embodiments of the sieve in the sieve insert.

In the embodiment shown in FIGS. 10 to 12 the sieve element 3 of the sieve insert 2 is arranged as a single leaf damper in the forward portion of the sieve insert the sieve element 3 being biased by means of a spring 13 to an active sieve position. An operating member 14 in the wall of the suction tube can be depressed externally in order to rotate the sieve 3 so that the function thereof will be more or less inhibited. In this embodiment this is possible only in the innermost position of the sieve insert, corresponding to full suction force. Other embodiments are of course possible within the scope of the accompanying claims. FIG. 13 disclose three different embodiments of the sieve which depending on the application can be used in order to limit to different degrees the ability of loose particles to pass the sieve element.

Figure 14:
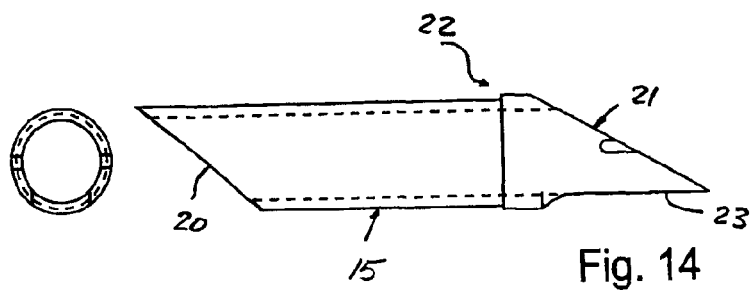
FIG. 14 is a side view of a sieve insert.
Figure 15:
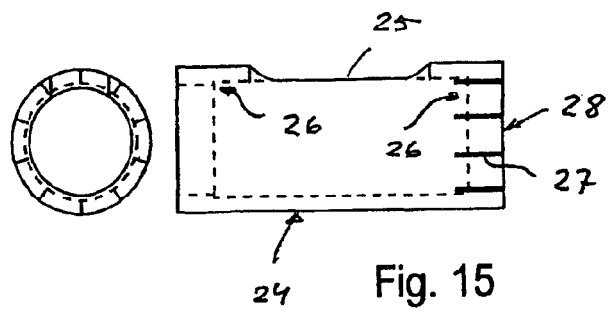
FIGS. 15 and 16 are side views of two elements forming part of the insert in FIG. 14.
Figure 16:
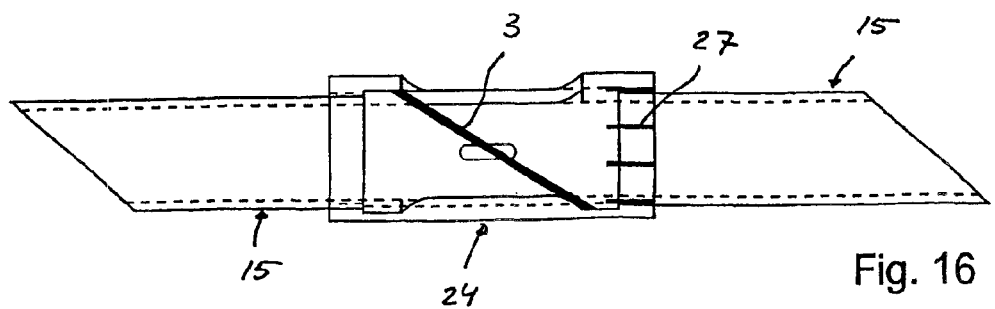

In FIGS. 14 and 15 there are shown details which together can form a suction tube insert of the kind shown in FIG. 16.

In FIG. 14 there is shown a tube element 15 the two ends 20 and 21 of which are cut obliquely. The end 21 differs to some extent from the end 20 by having a circumferential shoulder 22. On the side of the shoulder at the end 21 there is a recess 23 in the wall of the tube element 15. FIG. 15 discloses a substantially uniform socket 24 which has a centrally located wall recess 25, inner shoulders 26 and slots 27 at one end 28 thereof. The purpose is that two tube details of the type shown in FIG. 14 shall be interconnected by means of the socket according to FIG. 15 in order to form the unit according to FIG. 7. Thus, a tube element 15 is inserted into the socket 24 at the left end thereof as seen in the drawing. When this tube element has been inserted it can no longer be removed from the socket due to the presence of the shoulders 22, 26 on the two elements. Through the recess 25 a sieve element 3 formed in a suitable way for the intended application, is inserted the position thereof being fixed by a further tube element 15 inserted from the other end of socket 24. There is light slide fit between the tube elements and the socket 24 and, therefore, the socket can be rotated in relation to the tube elements 15 in order to provide a possibility, as in the embodiments previously described, to obtain a stray flux for control of the suction force. By the arrangement of slots 27 at the right end 28 of the socket as seen in the drawing it is possible after assemblence to separate one tube element 15 from the socket 24 if this is required for example for cleaning, which is contrary to the possibility at the other end.

The sieve insert 2 and the respective sieve elements shown in FIG. 13 can be simply produced in one piece by injection moulding. In that case two tool surfaces (core surfaces) are moved against each other. Grooves are made in one surface or in both surfaces. The groove pattern can be varied indefinitely. In one embodiment the grooves are perpendicular to each other engaging one surface or both surfaces. This provides a possibility to inject plastics or another material in the grooves at the same time as the tool surfaces meet each other at such great precision that there will be no room for material between these surfaces. Then, a grid- or sieve-like pattern will be obtained the design of which, i.e. the width and depth of the grooves and the mutual spacing thereof, is dependent of the size and shape of the contact surfaces. By variation of the design it is possible to obtain round, square, oval or rhombic apertures which can be distributed over the sieve/grid so that this is impermeable in some sectors and completely opened in others.

What is claimed is:

1. A device comprising:
   a suction tube open at both ends to be connected to a suction conduit for surgical or dental use for separating from the suction flow particulate material entrained therein;
   a sieve insert which is displaceable in the suction tube;
   a sieve element mounted to the sieve insert in an inclined position in relation to the axial direction of the suction tube; and
   a first aperture in the wall of the suction tube located behind the sieve element, the passage through said first aperature being controlled by the displaced position of the insert.

2. The device according to claim 1, wherein the sieve insert behind the sieve element forms a second aperture and is rotatable about the longitudinal axis of the suction tube to bring said first and second apertures to overlap to a major or minor degree in dependence of the rotational position of the sieve insert and thus to establish a major or minor stray flux through said first and second apertures.

3. The device according to claim 1, wherein the sieve insert has light slide fit in the suction tube.

4. The device according to claim 1, wherein the inner end of the sieve element as seen in the suction flow direction has an unperforated portion for collecting separated particulate material in a pocket formed between said portion and the inside surface of the suction tube.

5. The device according to claim 1, wherein an inlet muzzle is inclined in relation to the axial direction of the suction tube.

6. The device according to claim 1, wherein a muzzle of the suction tube or the separate sieve insert is intended to be held, at use thereof, substantially horizontally, the sieve element being arranged such that separated material will be collected in a pocket formed at the muzzle side at the lower portion of the sieve element.

7. The device according to claim 1, wherein said first aperture comprises a slot extending in the longitudinal direction of the suction tube, and further comprising a button penetrating the slot and being fixed to the sieve insert, the button together with the sieve insert being displaceable outwards and inwards in the suction tube to establish a major or minor stray flux through the slot.

8. The device according to claim 7, wherein the sieve element is transversely suspended in an inclined position by a spring blade and by means of the spring blade is biased towards a sieving position in the forward end of the sieve insert, the sieve element being rotatable under the influence of an operating member to an inactive position in which maximum and unlimited flow is allowed.

* * * * *